(12) United States Patent
Oishi et al.

(10) Patent No.: US 9,726,658 B2
(45) Date of Patent: Aug. 8, 2017

(54) DISPLAY DEVICE, DISPLAY METHOD, AND DISPLAY PROGRAM USED IN MEASUREMENT SYSTEM

(71) Applicant: SHIMADZU CORPORATION, Kyoto-shi, Kyoto (JP)

(72) Inventors: Akira Oishi, Kyoto (JP); Nobuya Hashizume, Kyoto (JP); Tomoaki Tsuda, Kyoto (JP); Masakazu Akechi, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 181 days.

(21) Appl. No.: 14/262,209

(22) Filed: Apr. 25, 2014

(65) Prior Publication Data

US 2015/0310584 A1  Oct. 29, 2015

(51) Int. Cl.
*G01N 33/49* (2006.01)
*G06T 3/20* (2006.01)
*G01N 23/20* (2006.01)
*G01N 35/00* (2006.01)

(52) U.S. Cl.
CPC ..... *G01N 33/491* (2013.01); *G01N 23/20008* (2013.01); *G01N 35/00* (2013.01); *G01N 2035/0091* (2013.01); *G01N 2201/06113* (2013.01); *G06T 3/20* (2013.01)

(58) Field of Classification Search
CPC .... G06T 3/20; G01N 23/20008; G01N 35/00; G01N 2035/0091; G01N 2201/06113
See application file for complete search history.

(56) References Cited

U.S. PATENT DOCUMENTS

2010/0294950 A1* 11/2010 Kitamura ............. A61B 5/1427
250/458.1

FOREIGN PATENT DOCUMENTS

| JP | 2005-108045 | | 4/2005 |
|---|---|---|---|
| JP | 2005108045 A | * | 4/2005 |
| JP | 2011-75420 A | | 4/2011 |
| WO | 2009/093306 A1 | | 7/2009 |

OTHER PUBLICATIONS

Japanese Office Action issued Jan. 6, 2014 in Japanese Patent Application No. 2011-244454.

* cited by examiner

*Primary Examiner* — Jwalant Amin
(74) *Attorney, Agent, or Firm* — Sughrue Mion, PLLC

(57) ABSTRACT

A display device, a display method, and a display program used in a measurement system capable of facilitating positioning in a measurement information image by displaying an IP (imaging plate) image having measurement information for β+ rays contained in blood to be measured and appending a guide G based on design information of a disc housing the blood to an IP image and displaying the image. The guide G is appended to an IP image in which a guide is not originally reflected, which makes it possible to visually discern a reference position (for example, the central position of the disc) in the IP image based on design information. As a result, it is possible to facilitate positioning in the IP image based on the guide G indicating the reference position (central position of the disc).

12 Claims, 10 Drawing Sheets

US 9,726,658 B2

DISPLAY DEVICE, DISPLAY METHOD, AND DISPLAY PROGRAM USED IN MEASUREMENT SYSTEM

This application incorporates by reference Japan Patent Publication No. 2013-101029, published May 23, 2013, made by the same inventors.

TECHNICAL FIELD

The present invention relates to a display device, a display method, and a display program used in a measurement system for measuring emitted light contained in a liquid to be measured, light generated from a fluorescent substance, or radiation contained in a liquid to be measured.

BACKGROUND ART

Measurement systems are used in liquid sampling devices, for example. A blood collection device for sampling blood—that is, collecting blood—will be described as an example of a liquid sampling device. Blood collection devices are used in quantitative analysis for nuclear medicine diagnosis (for example, PET (Positron Emission Tomography), SPECT (Single Photon Emission CT), or the like) and, in particular, are used in the measurement of radioactivity concentration in the arterial blood of small animals (for example, mice, rats, or the like).

Specifically, blood is sampled (collected) after a radioactive drug is administered to a small animal, and after plasma separation is performed by means of centrifugation following the completion of the entire blood collection at predetermined time intervals, changes in the radioactivity in whole blood and in plasma over time are measured (for example, see Literatures 1 and 2). More specifically, measurements are performed using an imaging plate (IP) which enables the visualization of radioactive distribution by exposing $\beta+$ rays contained in blood. An example of software for obtaining the value of the radiation dose from an IP image obtained from the imaging plate (abbreviated appropriately as "IP") is Multi Gauge produced by Fuji Photo Film Co., Ltd. With this software, the radiation dose per unit area can be determined by reading the IP image, setting the region of interest using software, and calculating the pixel value in the region of interest.

In Patent Literature 1, after a sample (here, blood) exposed to radiation is placed in a container segmented with prescribed dimensions, the radiation intensity of the sample is measured with an IP, and the area of the sample is measured with a scanner. Since the container is designed with prescribed dimensions, the volume of the sample is determined from the area of the sample reflected in the measurement results. Here, technology is disclosed in which the IP image of the radiation intensity obtained with the IP and the scanner image obtained with the scanner are combined, and the radiation concentration (=radiation intensity/volume) of each sample is calculated. In Patent Literature 2, an example of a container that is segmented with prescribed dimensions is described, and a container in which flow paths into which a plurality of samples are inserted are formed on a planar disc is illustrated.

When determining the radiation concentration in blood, superimposition processing such as that described below is performed. That is, superimposition processing is performed by superimposing an image of a disc imaged by a flat head scanner (scanner image) and a distribution image of $\beta+$ rays serving as counting information obtained with an IP (IP image). When this superimposition processing is performed with the software described above, the accurate alignment of the groove (flow path) positions of the disc and the plasma/blood cells can be realized by combining and superimposing the central position of the disc in the image of the disc with the central position of the disc in the $\beta+$ ray distribution image.

After the blood is centrifuged, the radiation contained in the plasma-separated plasma and blood cells is separated and counted, so the radiation concentration in plasma can be determined. In this way, the radiation concentration in blood per unit volume can be respectively determined by respectively dividing the radiation intensity of $\beta+$ rays of each part by the volume of each part from the counting information of the $\beta+$ rays of the portions overlapping the plasma and blood cells separated within the grooves (within the flow paths) on the $\beta+$ ray distribution image.

PRIOR ART LITERATURES (PATENT LITERATURE 1) International Patent Publication WO2009-093306
(PATENT LITERATURE 2) Japanese Unexamined Patent Application Publication 2011-075420

SUMMARY OF THE INVENTION

However, when the technologies disclosed in Patent Literatures 1 and 2 described above are combined, there is a problem in that positioning is difficult on the measurement information image (for example, an IP image).

That is, when determining the central position of the disc in the $\beta+$ ray distribution image, which is an IP image, the shape of the disc cannot be discerned from the distribution image, so it is difficult to determine the central position of the disc. If the central position of the disc is incorrect, it is necessary to perform processing to identify and align a plurality of grooves (flow paths) positions on the disc when performing superimposition processing on an image of the disc serving as a scanner image and a $\beta+$ ray distribution image serving as an IP image, which leads to the risk that processing may become complicated.

In addition, if the grooves (flow paths) are mistaken, there is a risk of mistakenly determining the radiation concentration by dividing the radiation intensity of a flow path differing from the flow path to be determined by the volume or by dividing the radiation intensity by the volume in a flow path differing from the flow path to be determined. In this way, when a reference position for positioning (for example, the central position of the disc) cannot be discerned in a measurement information image such as an IP image or the like obtained with an IP, superimposition processing becomes complicated, or data such as the radiation concentration is determined in error.

The present invention was conceived in light of such circumstances, and the object of the present invention is to provide a display device, a display method, and a display program used in a measurement system capable of facilitating positioning in a measurement information image.

The present inventors obtained the following such knowledge as a result of conducting dedicated research in order to solve the problem described above.

Specifically, the positions of flow paths can be individually identified by fixing the container with a fixture or the like while positioning and supporting the container, providing notches or protuberances in the container, or marking the container (for example, attaching a separate substance to the container, engraving symbols or numbers into the container, or providing a member with a symbol or number pattern in a protruding state on the container). In actuality, a scanner image obtained with a scanner is a morphological information image having the morphological information of the container including the sample, so information such as notches, protuberances, or markers is reflected in the image. However, it was ascertained that since an IP image obtained with an IP is a measurement information image having radiation measurement information, information such as notches, protuberances, or markers is not reflected in the image.

When the container is fixed with a fixture or the like while being positioned and supported, the flow paths are also fixed, so the flow paths can be individually identified between the IP image and the scanner image.

On the other hand, the containers used in Patent Literatures 1 and 2 described above are discs provided with 36 flow paths, so the angles of flow paths adjacent to one another are 360°/36 paths=10°/path. Accordingly, even if a fixture and technology for visualizing and displaying images are combined, the angle is only 10°, and it is not easy to individually identify as many as 36 designed flow paths. Even if a fixture and technology for visualizing and displaying images are combined, when there is deviation in the angle between the respective images at the time of display, it is necessary to calibrate the angle (calibration). In addition, even if the respective images are overlaid to enable superimposed display, it may not be noticed that the flow paths are displayed with deviation in the angles, and adjacent flow paths may be superimposed and displayed in a state with deviation in the angles thereof.

Further, even if a fixture and technology for visualizing and displaying images are combined, although information such as notches, protuberances, or markers (identification information) is reflected in the scanner image, these types of identification information are still not reflected in the IP image. Therefore, in addition to technology for visualizing and displaying images, the present inventors obtained the knowledge that by appending a guide indicating a specific position or a reference position to a measurement information image such as an IP image and displaying the image, it is possible to display the guide in a measurement image such as an IP image in addition to a morphological information image such as a scanner image, and that this facilitates positioning in the measurement information image, regardless of the presence or absence of a fixture.

The present invention, which is based on such knowledge, assumes the following such configuration.

Specifically, the display device used in a measurement system according to the present invention is a display device used in a measurement system for measuring emitted light contained in a liquid to be measured, light generated from a fluorescent substance, or radiation contained in a liquid to be measured, the display device being equipped with a guide display for displaying a measurement information image having measurement information for emitted light contained in the liquid to be measured, light generated from a fluorescent substance, or radiation contained in the liquid to be measured and appending a guide, which is based on region information of the region to be measured serving as the specific position to be measured or design information of a container housing a liquid to be measured, to the measurement information image and displaying the image.

(OPERATION/EFFECT) With the display information used in a measurement system according to the present invention, by providing a guide display for displaying a measurement information image having measurement information for emitted light contained in the liquid to be measured, light generated from a fluorescent substance, or radiation contained in the liquid to be measured and appending a guide, which is based on region information of the region to be measured serving as the specific position to be measured or design information of a container housing a liquid to be measured, to the measurement information image and displaying the image, a guide is appended to a measurement information image in which a guide is not originally reflected, which makes it possible to visually discern a specific position or a reference position based on design information in the measurement information image. As a result, it is possible to facilitate positioning in the measurement information image based on the guide indicating the specific position or reference position.

In addition, the display method of the present invention is a display method for displaying measurement data obtained by measuring emitted light contained in a liquid to be measured, light generated from a fluorescent substance, or radiation contained in a liquid to be measured, the method comprising a guide display step for displaying a measurement information image having measurement information for emitted light contained in the liquid to be measured, light generated from a fluorescent substance, or radiation contained in the liquid to be measured and appending a guide, which is based on region information of the region to be measured serving as the specific position to be measured or design information of a container housing a liquid to be measured, to the measurement information image and displaying the image.

In addition, the display program of the present invention is a display program for making a computer execute a series of processes for displaying measurement data obtained by measuring emitted light contained in a liquid to be measured, light generated from a fluorescent substance, or radiation contained in a liquid to be measured, the program comprising a guide display step for displaying a measurement information image having measurement information for emitted light contained in the liquid to be measured, light generated from a fluorescent substance, or radiation contained in the liquid to be measured and appending a guide, which is based on region information of the region to be measured serving as the specific position to be measured or design information of a container housing a liquid to be measured, to the measurement information image and displaying the image.

(OPERATION/EFFECT) With the display method and display program of the present invention, a measurement information image having measurement information for emitted light contained in a liquid to be measured, light generated from a fluorescent substance, or radiation contained in a liquid to be measured is displayed in the guide display step, and a guide, which is based on region information of the region to be measured serving as the specific position to be measured or design information of a container housing a liquid to be measured, is appended to the measurement information image and displayed so that a specific position or a reference position based on design information can be visually discerned in the measurement information image. As a result, it is possible to facilitate positioning in the measurement information image based on the guide indicating the specific position or reference position.

The display device described above is preferably equipped with an image/guide adjustor for moving and adjusting at least one of either a measurement information image or a guide on a display screen or adjusting the size of one or the other on the display screen. In addition, the display method of the present invention described above preferably includes an image/guide adjustment step for moving and adjusting at least one of either a measurement information image or a guide on a display screen or adjusting the size of one or the other on the display screen. By making adjustments on the display screen, it is possible to relatively align the measurement information image with respect to the guide, and even in superimposition processing with the morphological information image described above, superimposition processing can be performed accurately after the positions are aligned.

In addition, when the container is a disc, the guide is preferably a guide with a circular shape or a shape similar to a circular shape. By using a guide that conforms to the shape of a circular container, it is possible to further facilitate positioning in the measurement information image.

Further, when the grooves (flow paths) of the container provided in order to house the liquid to be measured extend linearly, the guide is preferably a linear guide with the same angles as the linear grooves of the container in question. Since the number of grooves or the angles thereof are known from the design information of the container, using a guide that conforms to the shape of the linear grooves makes it possible to further facilitate positioning in the measurement information image.

In addition, the guide may also be a guide with a contour of the same shape as the grooves of the container provided in order to house the liquid to be measured. By using a guide that conforms to the contour of the grooves, it is possible to further facilitate positioning in the measurement information image. In addition, the guide may also be a linear guide passing through the central position of the container. In this case, positioning in the measurement information image can be performed using the central position as a reference position.

EFFECT OF THE INVENTION

With the display information used in a measurement system according to the present invention, by providing a guide display for displaying a measurement information image having measurement information for emitted light contained in the liquid to be measured, light generated from a fluorescent substance, or radiation contained in the liquid to be measured and appending a guide, which is based on region information of the region to be measured serving as the specific position to be measured or design information of a container housing a liquid to be measured, to the measurement information image and displaying the image, it is possible to facilitate positioning in the measurement information image based on a guide indicating a specific position or a reference position.

In addition, with the display method and display program of the present invention, a measurement information image having measurement information for emitted light contained in a liquid to be measured, light generated from a fluorescent substance, or radiation contained in a liquid to be measured is displayed in the guide display step, and a guide, which is based on region information of the region to be measured serving as the specific position to be measured or design information of a container housing a liquid to be measured, is appended to the measurement information image and displayed, which makes it possible to facilitate positioning in the measurement information image based on a guide indicating a specific position or a reference position.

DETAILED DESCRIPTION OF THE EXEMPLARY EMBODIMENTS

An embodiment of the present invention will be described hereinafter with reference to the drawings.

Figure 1:
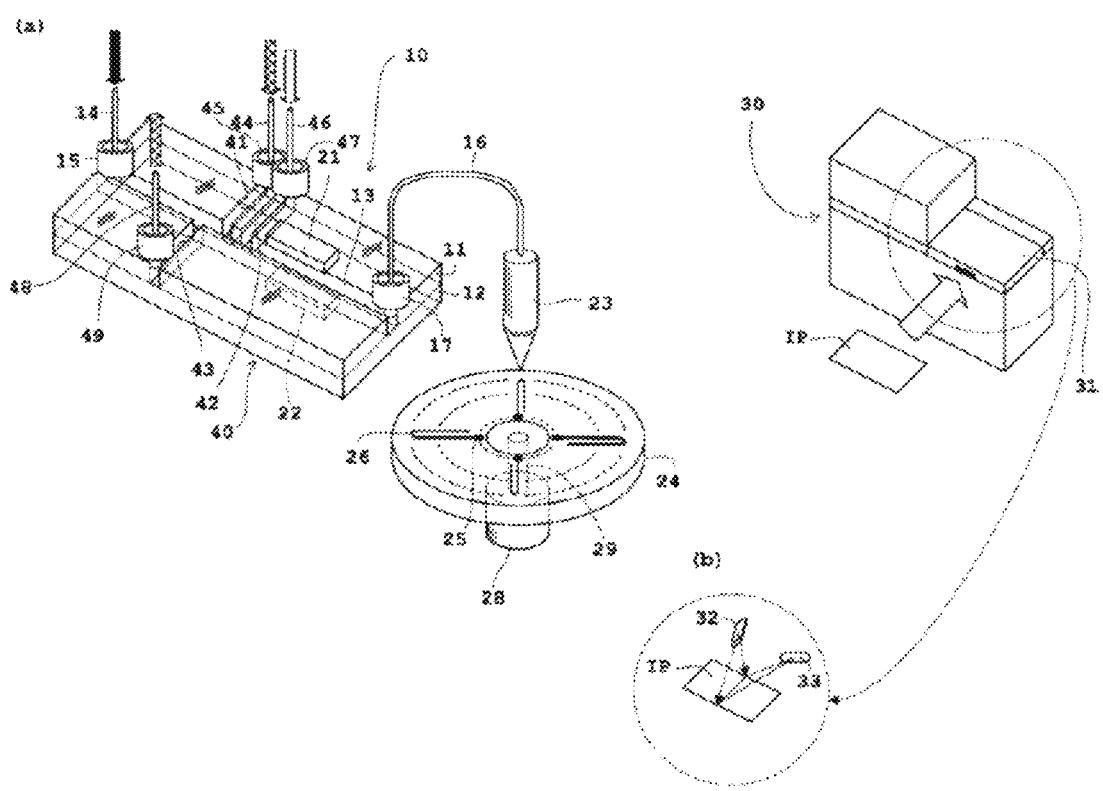
FIG. 1 is a schematic perspective view of a blood collection device and a measurement device in an embodiment.
Figure 2:
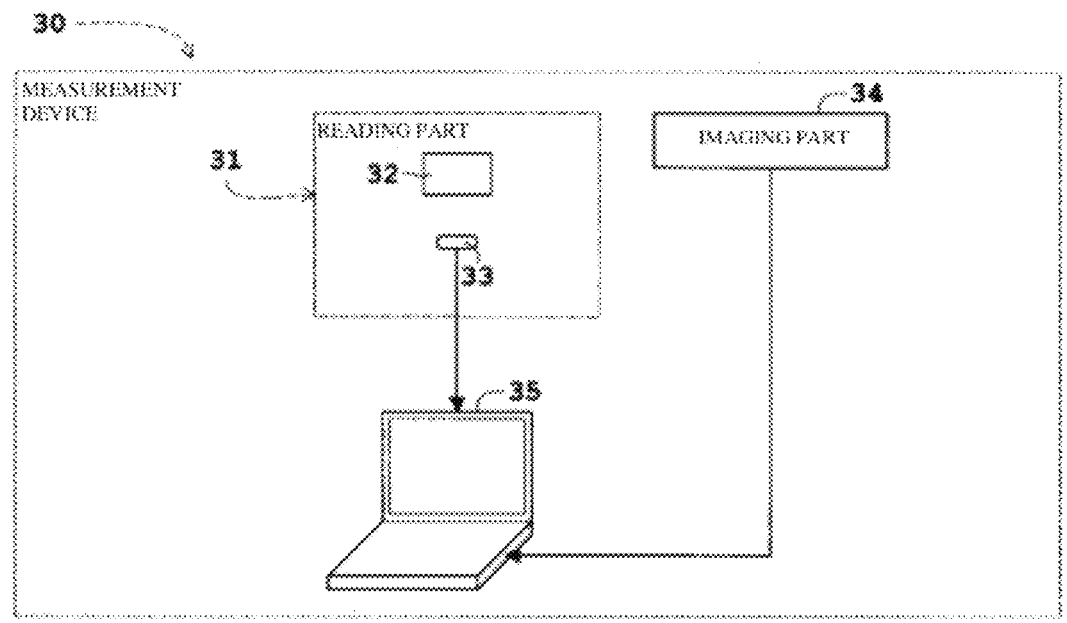
FIG. 2 is a block diagram of the measurement device in the embodiment.
Figure 3:
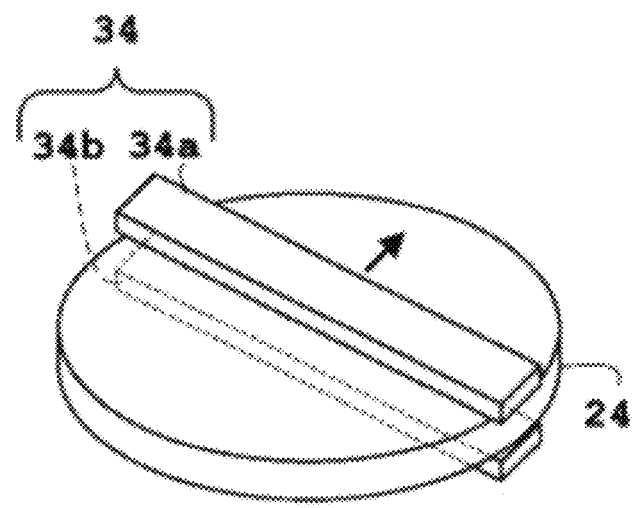
FIG. 3 is a schematic perspective view of a scanner in the imaging part of the measurement device.

FIG. 1 is a schematic perspective view of a blood collection device and a measurement device in an embodiment, and FIG. 2 is a block diagram of the measurement device in the embodiment. FIG. 3 is a schematic perspective view of a scanner in the imaging part of the measurement device. This embodiment will be described using blood as an example of a liquid to be measured and using a system equipped with a blood collection device and a measurement device as an example of a measurement system.

As illustrated in FIG. 1, a blood collection device 10 of this embodiment separates and samples blood to be measured in a time series. In addition, a measurement device 30 for measuring radiation (for example, $\beta$ rays, $\gamma$ rays, or the like) contained in the blood collected by the blood collection device 10 is provided in the vicinity of the blood collection device 10.

The blood collection device 10 is equipped with a microfluid element (liquid separating device) 40 configured by layering two PDMS substrates 11 and 12 consisting of a PDMS resin (polydimethylsiloxane) vertically. Groove machining is performed with prescribed dimensions on the PDMS substrates 11 and 12, and a main flow path 13 and side paths 41, 42, and 43 are respectively formed by the grooves of this groove machining. Here, the material of the blood collection device 10 is not limited to PDMS, and any resin such as an acryl, polycarbonate, or COP (cycloolefin polymer) may be used as long as the material is optically transparent.

A catheter 14 is disposed on the blood inlet side of the main flow path 13, and the main flow path 13 and the catheter 14 are connected via a connector 15. Blood is continuously feed from the catheter 14 into the main flow path 13, and the flow rate is controlled with a valve (not illustrated). A blood tube 16 is disposed on the blood outlet side of the main flow path 13, and the main flow path 13 and the blood tube 16 are connected via a connector 17.

A light source 21 and a photodiode 22 are disposed so as to sandwich the main flow path 13. Blood flowing through the main flow path 13 or a heparin solution described below is irradiated with light from the light source 21, and the photodiode 22 detects the blockage of light by the blood so as to measure the length information of the blood or the heparin solution described below while optically monitoring the blood or heparin solution. Here, the device was described using the light source 21 and the photodiode 22 as an optical measurement means, but the means is not limited to the light source 21 and the photodiode 22 as long as the means measures the spacing of the liquid while optically monitoring the liquid to be measured. For example, volume information of the liquid to be measured may be obtained by a CCD camera. In addition, the light source 21 and the photodiode 22 are disposed opposite one another so as to sandwich the main flow path 13, as illustrated in FIG. 1, resulting in a so-called "transmissive sensor" which detects light blockage by blood, but an optical detector such as a photodiode may be disposed on the same side as the light source so as to form a so-called "reflective sensor" which detects light reflected by blood.

On the other hand, a nozzle 23 is connected to the downstream side of the blood tube 16 described above. A capillary tube such as an injection needle or a glass tube is used as the nozzle 23. Here, the nozzle 23 is used as a discharge part for discharging the liquid, but a dispenser may also be used. A disc (also called a "CD well") 24 is disposed so as to receive and house blood dripping down from the nozzle 23. A plurality of flow path inlets 25 (see also FIG. 4) consisting of a plurality of opening parts for receiving dropped blood are disposed radially on the central side of the disc 24. As in the case of the PDMS substrates 11 and 12 described above, the disc 24 is also subjected to groove machining, and a plurality of U-shaped flow paths 26 (see also FIG. 4) consisting of U-shaped grooves are formed radially by the grooves of this groove machining. Each U-shaped flow path 26 is respectively connected one-to-one to the outer end of each flow path inlet 25 described above, and each U-shaped flow path 26 is formed so as to extend in the radial direction of the disc 24. By interposing the nozzle 23 in this way, the disc 24 is formed so that blood can flow through the main flow path 13. The disc 24 corresponds to the container in the present invention, and the U-shaped flow paths 26 correspond to the grooves in the present invention. The specific configuration of the disc 24 will be described below with reference to the drawings beginning with FIG. 4.

On the other hand, the measurement device 30 is equipped with a reading part 31. This reading part 31 is provided with a cover part for inserting an exposed imaging plate IP, and the reading part 31 detects β+ rays contained in the blood by reading excited light from the imaging plate IP. Specifically, as illustrated in FIG. 1(b), the reading part 31 is equipped with a laser light source 32 and a photomultiplier tube (photomultiplier tube [different spelling in Japanese for clarification]) 33. The imaging plate IP is irradiated with a laser from the laser light source 32, and the photomultiplier tube 33 converts light excited by the laser irradiation of the imaging plate IP to electrons and multiplies the light so as to two-dimensionally and simultaneously detect β+ rays.

Next, a block diagram of the measurement device 30 will be described. As illustrated in FIG. 2, the measurement device 30 is equipped with an imaging part 34 and a display device 35 in addition to the reading part 31 described above. The display device 35 may consist of an ordinary personal computer. The display device 35 corresponds to the display device in the present invention. The specific configuration of the display device 35 will be described below with reference to the drawings beginning with FIG. 5.

As illustrated in FIG. 3, the imaging part 34 images the disc 24. In this embodiment, a flat head scanner is used as the imaging part 34. The flat head scanner consists of a linear light source 34a having a length at least equal to the diameter of the disc 24 and a linear photodiode array (that is, a line sensor) 34b disposed opposite the light source 34a so as to sandwich the disc 24. The disc 24 is imaged by scanning (scanning [different spelling in Japanese for clarification]) the disc 24 with the flat head scanner, and an image of the disc 24 is thus obtained.

Returning to the explanation of FIG. 1, as described above, the micro-fluid element 40 is equipped with a main flow path 13 for feeding blood, a side path 41 for feeding a heparin solution, which is a type of an anticoagulant for preventing the occurrence of blood coagulation, a side path 42 for feeding air or a gas, and a side path 43 for discharging the blood or heparin solution.

A washing solution tube 44 is disposed on the solution inlet side of the side path 41, and the side path 41 and the washing solution tube 44 are connected via a connector 45. The flow paths are washed as necessary by pathing a heparin solution into the main flow path 13 from the washing solution tube 44 via the side path 41. The flow rate of the heparin solution is controlled with a valve. The anticoagulant is not limited to a heparin solution.

An air bubble tube 46 is disposed on the gas inlet side of the side path 42, and the side path 42 and the air bubble tube 46 are connected via a connector 47. The inflow time of air or gas controlled with a pressure generator (not illustrated) is adjusted with a valve, and air or a gas is fed into the main flow path 13 via the side path 42. These air bubbles are used to extract blood based on the length information of the blood and to discharge liquid waste (blood, the heparin solution, or a mixture thereof) remaining in the flow paths of the micro-fluid element 40. Here, the gas that is fed is not limited, and any gas that does not react with blood or the heparin solution may be used, as exemplified by a noble gas such as helium, neon, or argon or nitrogen gas.

The air bubble tube 46 feeds a gas (for example, air or a gas) into the main flow path 13 via the side path 14, and the gas is inserted as air bubbles at designated, prescribed intervals so as to separate the blood to be measured in a time series and feed the blood to the disc 24. That is, the air bubbles fulfill the function of a separator. Here, a gas was used as a separator, but the separator is not limited to a gas, but a liquid other than the liquid to be measured may also be used as a separator as long as there is little or no possibility that the liquid will mix with the liquid to be measured (blood in this embodiment). When the liquid to be measured is blood, as in the case of this embodiment, a liquid that does not mix with blood such as a mineral oil or a fluorine-based oil may be used as a separator. However, when a liquid is used as a separator, the liquid can be used as a separator since it comes into contact with the blood, but this is not preferable from the perspective that the liquid is fed to the disc 24 and collected.

A liquid waste tube 48 is disposed on the liquid waste outlet side of the side path 43, and the side path 43 and the liquid waste tube 48 are connected via a connector 49. The discharge rate is adjusted with a valve, and blood other than the blood to be collected, the heparin solution after the flow paths are washed, or a mixture thereof is discharged as liquid waste.

In addition, a valve is disposed further downstream from the connector 15 of the main flow path 13, and a valve is disposed further upstream from the connector 17 of the main flow path 13, the light source 21, and the photodiode 22. A valve is disposed further downstream from the connector 45 of the side path 41, and a valve is disposed further downstream from the connector 47 of the side path 42. In addition, a valve is disposed further upstream from the connector 49 of the side path 43.

Figure 4:
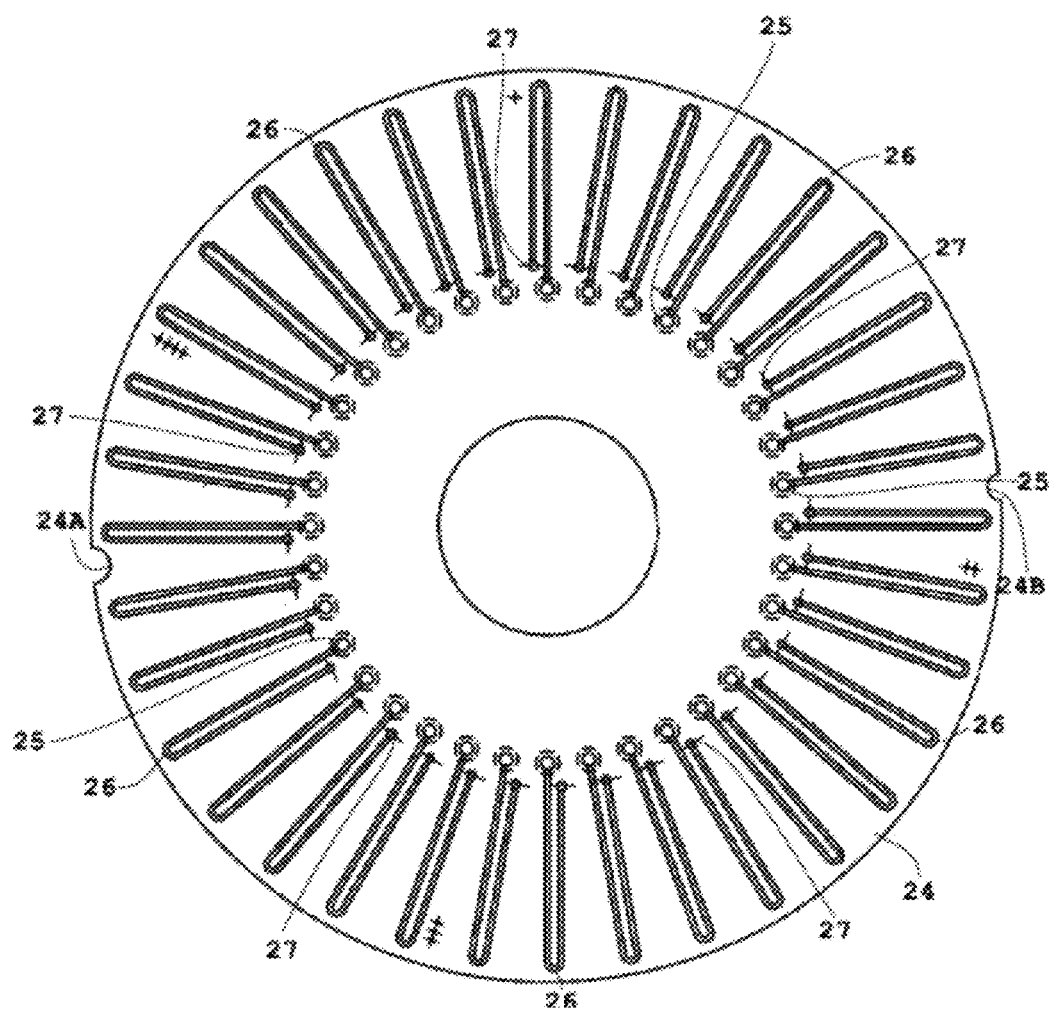
FIG. 4 is a schematic plan view of a disc in the embodiment.

Next, the specific configuration of the disc 24 will be described with reference to FIGS. 1 and 4. FIG. 4 is a schematic plan view of the disc in the embodiment. As illustrated in FIG. 4, the U-shaped flow paths 26 of the disc 24 are formed so as to connect the flow inlets 25 described above and air holes 27. When the flow paths 26 serving as introduction ports for blood is defined as the upstream part of the blood and the air holes 27 are defined as the downstream part, the U-shaped flow paths 26 extend from the inside toward the outside in the radial direction of the disc 24 from the upstream part to the downstream part and then fold back and extend from the outside toward the inside in the radial direction of the disc 24 to form a U shape. A plurality of these U-shaped flow paths 26 is provided.

Excluding the folded parts, the U-shaped flow paths 26 are linear grooves formed so as to extend from the inside toward the outside in the radial direction of the disc 24 and are also linear grooves formed so as to extend from the outside toward the inside in the radial direction of the disc 24. The respective folded portions are positioned on a circular trajectory similar to that of the disc 24, and the circle drawn by this circular trajectory can be considered a circle with a radius equal to the distance from the center of the disc 24 to the end of the folded portions. Similarly, the respective flow path inlets 25 (opening parts) are also positioned on a circular trajectory similar to that of the disc 24, and the circle drawn by this circular trajectory can be considered a circle with a radius equal to the distance to the inside ends of the flow path inlets 25 of the disc 24.

The disc 24 has depressions 24A and 24B in two locations, and these depressions are engaged with a fixture 61 described below (see FIG. 7). The fixture 61 will be described below with reference to the drawings beginning with FIG. 7.

As illustrated in FIG. 1, a motor 28 for rotating the disc 24 is provided in the center of the disc 24. A rotary shaft 29 of the motor 28 is connected to the disc 24 so that the centrifugal force of the disc 24 caused by the motor 28 can be utilized to perform plasma separation to separate the blood into plasma and blood cells by means of centrifugation.

In this embodiment, the disc 24 is formed from an acrylic plate. The material of the disc 24 is not limited to an acrylic material, and any resin such as an acryl, polycarbonate, or COP may be used in addition to the PDMS described above as long as the material is optically transparent.

Figure 5:
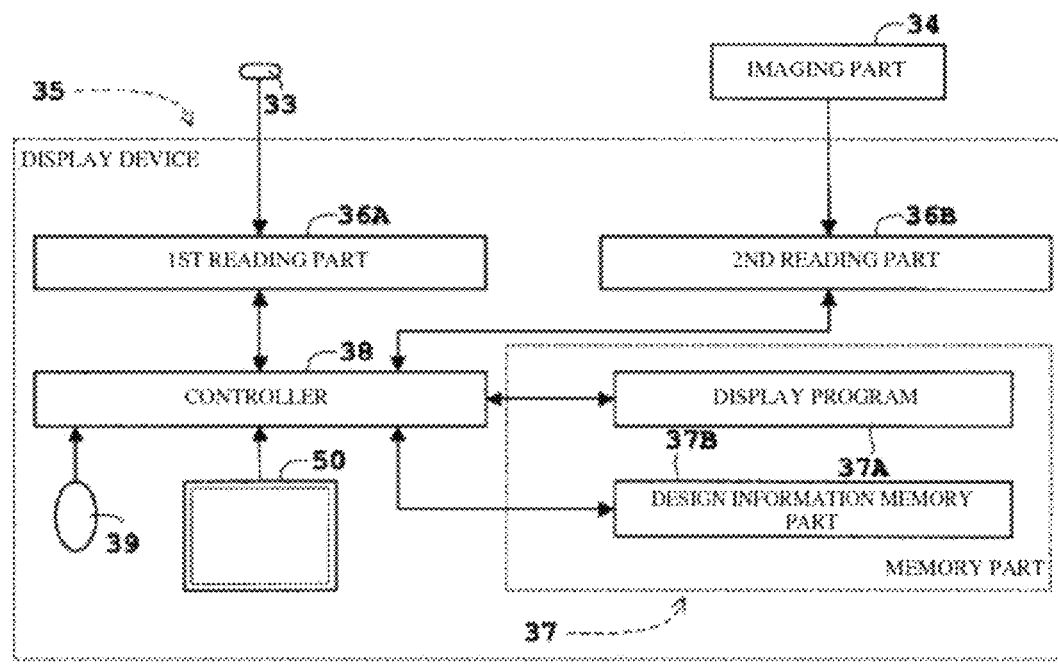
FIG. 5 is a block diagram of a display device in the embodiment.
Figure 6:
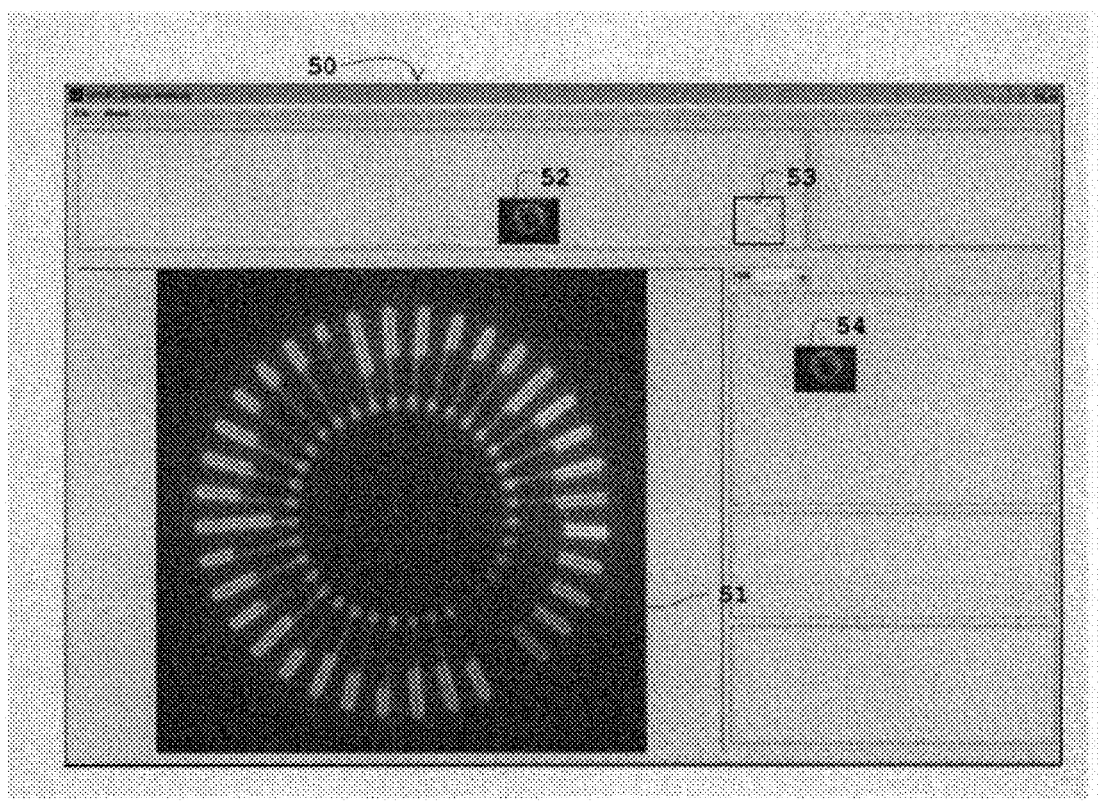
FIG. 6 is an example of the display format of the output monitor of the display device.

Next, the specific configuration of the display device 35 will be described with reference to FIGS. 5 and 6. FIG. 5 is a block diagram of the display device in this embodiment, and FIG. 6 is an example of the display format of the output monitor of the display device. As illustrated in FIG. 5, the display device 35 is equipped with a first reading part 36A, a second reading part 36B, a memory part 37, a controller 38, an input part 39, and an output monitor 50. The controller 38 corresponds to the superimposition processor in the present invention, and the input part 39 corresponds to the image/guide adjustor in the present invention.

The first reading part 36A and the second reading part 36B consist of reading devices such as I/O (input/output) devices, for example. The first reading part 36A reads an IP image obtained by the imaging plate IP (see FIG. 1) via the reading part 31 (see FIG. 1 or 2). The second reading part 36B reads a scanner image obtained by the imaging part 34. The IP image corresponds to the measurement information image in the present invention, and the scanner image corresponds to the morphological information image in the present invention.

The memory part 37 consists of a storage medium such as a ROM (read-only memory) or a RAM (random access memory). In this embodiment, the memory part 37 is equipped with a display program 37A for making a computer (controller 38 in this embodiment) execute the series of processes illustrated in FIG. 11 and a design information memory part 37B for storing design information of the container (disc 24 in this embodiment; see FIG. 1, 3, or 4) for housing the liquid to be measured (blood in this embodiment). The display program 37A consists of a ROM, and the design information memory part 37B consists of a RAM. In this embodiment, a circle of the same size as the disc 24, a circle with a radius equal to the distance from the center of the disc 24 described above to the end of the folded portion, a circle with a radius equal to the distance to the inside end of the flow path inlets 25 (see FIG. 1 or 4) of the disc 24 described above, the number (36 in this embodiment) or angle (10° in this embodiment) of the U-shaped flow paths 26 (see FIG. 1 or 4) consisting of two linear grooves and folded portions, and the crossed lines consisting of a line passing through the central position of the disc 24 and a line orthogonal to this line passing through the central position are used as examples of design information. The display program 37A corresponds to the display program in the present invention.

The controller 38 consists of a central processing unit (CPU) or the like. The controller 38 executes a program for performing various types of image processing, a program for calculating the radiation concentration, and the display program 37A illustrated in FIG. 5 so as to perform image processing corresponding to the programs or the series of processes illustrated in FIG. 11 corresponding to the display program 37A (reading control for the first/second reading parts 36A and 36B, display mode of the output monitor 50). As various types of image processing, the controller 38 has a reduction/enlargement processing function for performing reduction processing or enlargement processing on the scanner image and a contour intensifying function for intensifying the contour of the scanner image and outputting a contour-intensified image.

The input part 39 consists of a pointing device or the like such as a mouse, a keyboard, a joystick, a track ball, or a touch panel. In this embodiment, the input part 39 has an image selection function for selecting each image displayed in a reduced form on reduced screens 52, 53, and 54 described below (see FIG. 6) in order to display an image in an enlarged form on the main screen 51 described below (see FIG. 6) or a function of an image/guide adjustor for adjusting an image by moving at least one of either the measurement information image (an IP image in this embodiment) or a guide G described below (see FIGS. 8 to 10) on the display screen or adjusting the size of one or the other on the display screen.

As illustrated in FIG. 6, the output monitor 50 is equipped with a main screen 51 for displaying the main image in an enlarged form, a reduced screen 52 for displaying the IP image in a reduced form, a reduced screen 53 for displaying the scanner image in a reduced form, and a reduced screen 54 for displaying the superimposed image formed by overlaying the IP image and the scanner image and performing superimposition processing in a reduced form. In FIG. 6, the IP image read by the first reading part 36A and the scanner image read by the second reading part 36B are overlaid and displayed in a superimposed form on the main screen 51. On the main screen 51, a guide G (see FIGS. 8 to 10) is appended to the IP image and displayed. The main screen 51 corresponds to the guide display in the present invention.

Next, the specific configuration of the fixture 61 will be described with reference to FIG. 7. FIG. 7 is a schematic plan view of the fixture in the embodiment. As illustrated in FIG. 7, the fixture 61 is provided in order to fix the disc 24 (see FIG. 1, 3, or 4) while positioning and supporting the disc. The fixture 61 is provided with an opening part 62 with which the disc 24 engages, and two protuberances 62A and 62B are provided in this opening part 62. The depression 24A of the disc 24 (see FIG. 4) engages with the protuberance 62A, and the depression 24B of the disc 24 (see FIG. 4) engages with the protuberance 62B so that the fixture 61 fixes the disc 24 while positioning and supporting the disc.

Figure 7:
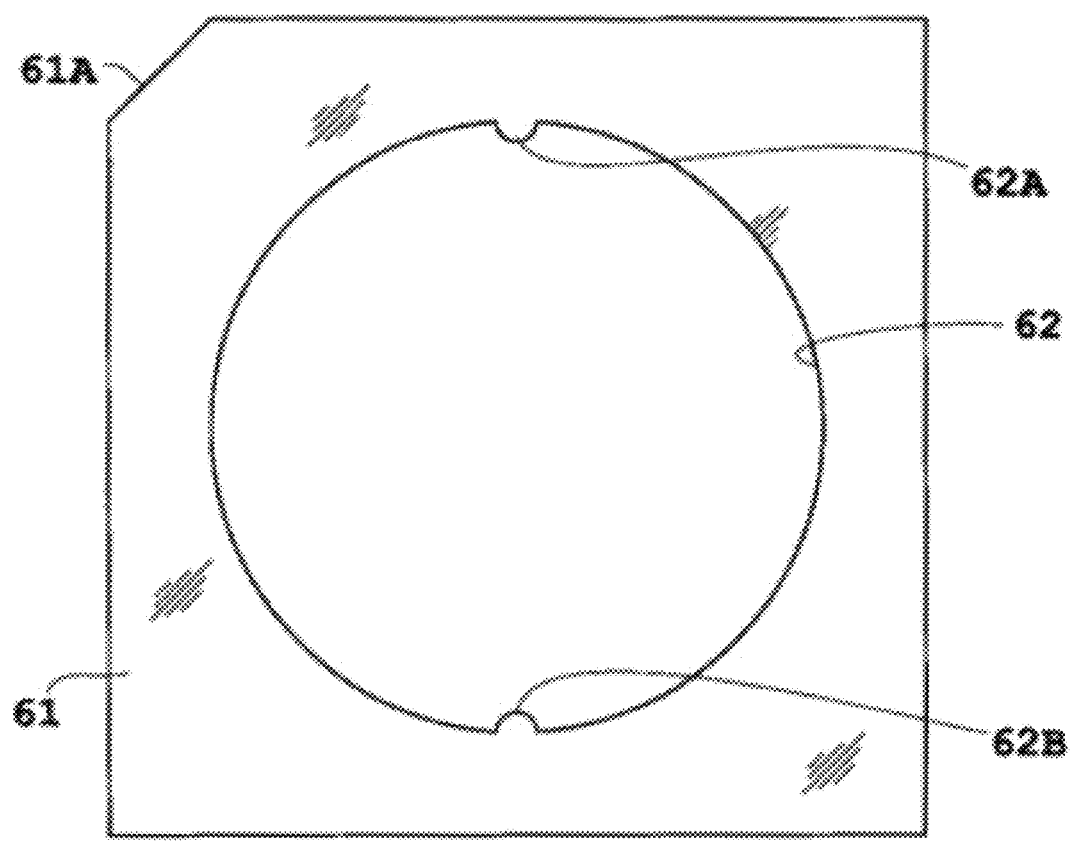
FIG. 7 is a schematic plan view of a fixture in the embodiment.

In this embodiment, as illustrated in FIG. 7, one opening part 62 is provided, and one disc 24 is fixed by one fixture 61, but the device may also be configured so that a plurality (two, for example) of opening parts 62 are provided and a plurality of discs 24 are fixed to one fixture 61. In addition, a notch 61A is provided to the fixture 61 in the upper left part of the drawing.

In the case of the fixture 61 illustrated in FIG. 7, there is a risk that the vertical and horizontal directions may be mistaken due to the symmetry of the flow path inlets 26 (see FIG. 1 or 4) when rotated by 180°, but by providing the notch 61A in the upper left part of the drawing, it is possible to align the orientations of the IP image obtained by the imaging plate IP (see FIG. 1) and the scanner image obtained by the imaging part 34 via the reading part 31 (see FIG. 1 or 2) using the notch 61A as a reference.

The fixture 61 fixes, positions, and supports the disc 24 that is plasma-separated into plasma and blood cells by the centrifugal force of the disc 24 (see FIG. 1, 3, or 4) caused by the motor 28 (see FIG. 1), and the orientation or position of each of the flow path inlets 26 of the disc 24 (see FIG. 1 or 4) is also fixed as a result. In the state in which the orientation or position is fixed, an IP image is obtained by imaging the disc 24 using the imaging plate IP (see FIG. 1), and a scanner image is obtained by imaging the disc 24 with the flat head scanner of the imaging part 34 (see FIG. 2, 3, or 5). The order of imaging is not particularly limited.

Specifically, using the disc 24 (see FIG. 1, 3, or 4) and the fixture 61 as samples, a cassette not illustrated in the drawings is opened and housed, and after the imaging plate IP (see FIG. 1) is housed thereon, the cassette is closed and exposed. As a result of this exposure, electrons are captured in the lattice defects of a fluorescent substance (not illustrated) of the imaging plate IP due to the ionization power of the β+ rays contained in the blood. After exposure for a certain amount of time, the imaging plate IP is retrieved from the cassette and inserted into the cover part of the reading part 31 (see FIG. 1 or 2) of the measurement device 30 (see FIG. 1). The imaging plate IP is then irradiated with light and exposed.

The imaging plate IP (see FIG. 1) is irradiated with a laser from the laser light source 32 (see FIG. 1 or 2) of the reading part 31 (see FIG. 1 or 2). The captured electrons are excited to a conductive state by this irradiation and recombined with the positive holes so as to be excited as light from the fluorescent substance. The light excited by the laser irradiation of the imaging plate IP is converted to electrons and multiplied by the photomultiplier tube 33 (see FIG. 1, 2, or 5), and the light is thus two-dimensionally and simultaneously detected and counted as electrical pulses. After the imaging plate IP is irradiated from the laser light source 32, the captured electrons are eliminated by irradiating the imaging plate IP with light from an elimination light source (not illustrated) in order to reuse the imaging plate IP. The radiation dose in the blood, which β+ ray counting information, is determined based on the β+ ray counting information determined by the imaging plate IP and the reading part 31. An IP image is obtained in this manner.

On the other hand, the imaging part 34 (see FIG. 2, 3, or 5) images the plasma-separated plasma and blood cells for each disc 24 (see FIGS. 1, 3, and 4) and fixture 61 supporting the disc 24. As a result of irradiation with light from the light source 32a (see FIG. 3) of the flat head scanner of the imaging part 34, plasma and blood cells appear as differences in density in the captured image due to differences in absorbance and can therefore be easily identified in the image. A scanner image is obtained in this manner.

The scanner image is a morphological information image including blood, the disc 24 (see FIG. 1, 3, or 4), or the fixture 61 provided with the notch 61A, so information such as the notch 61A is also reflected in the image, but the IP image is a measurement information image having measurement information, so information such as the notch 61A is not reflected in the image. However, since the orientation or position of each flow path inlet 26 (see FIG. 1 or 4) is fixed by the fixture 61, the relative positions of the U-shaped flow paths 26 of the disc 24 (which are fixed positions on the disc 24) and the fixture 61 are also determined.

However, even if the fixture 61 is provided, misalignment occurs between the IP image and the scanner image to be subjected to superimposition processing if the disc 24 is inclined for each fixture 61 when the disc 24 (see FIG. 1, 3, or 4) is imaged with the flat scanner of the imaging part 34 (see FIG. 2, 3, or 5). As a result, there is a possibility that the images may be displayed with a misaligned angle even when the individual images are overlaid and displayed in a superimposed form.

Figure 8:
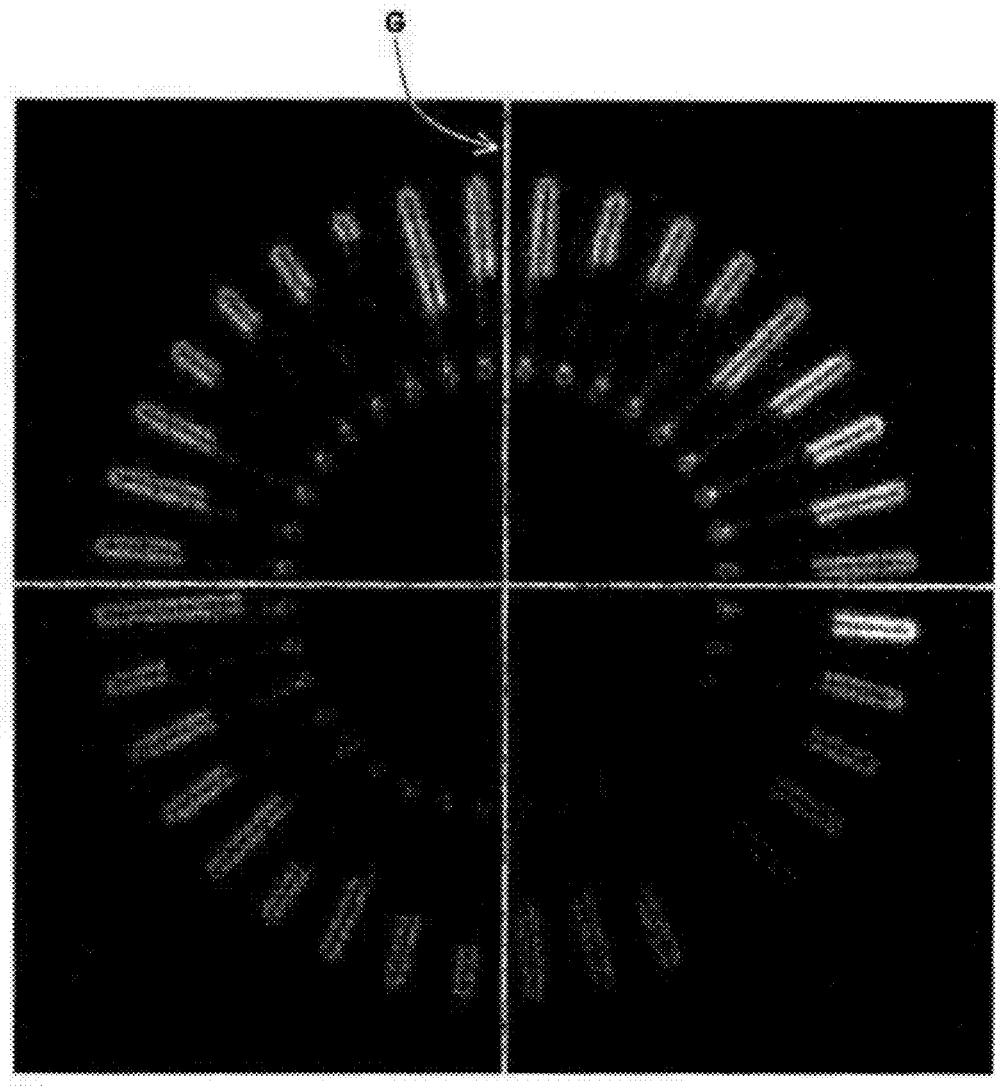
FIG. 8 is a diagram in which each example of the guide is appended to an IP image.
Figure 9:
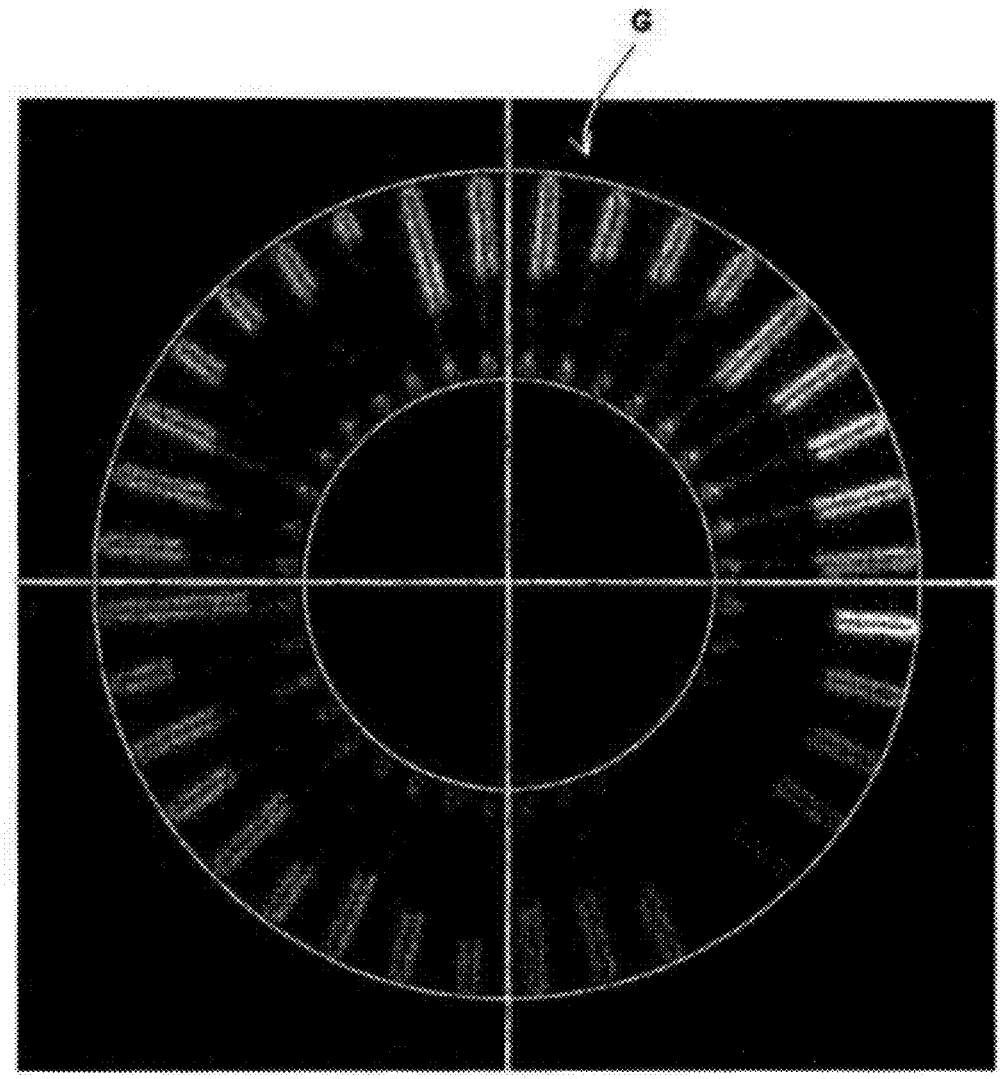
FIG. 9 is a diagram in which each example of the guide is appended to an IP image.
Figure 10:
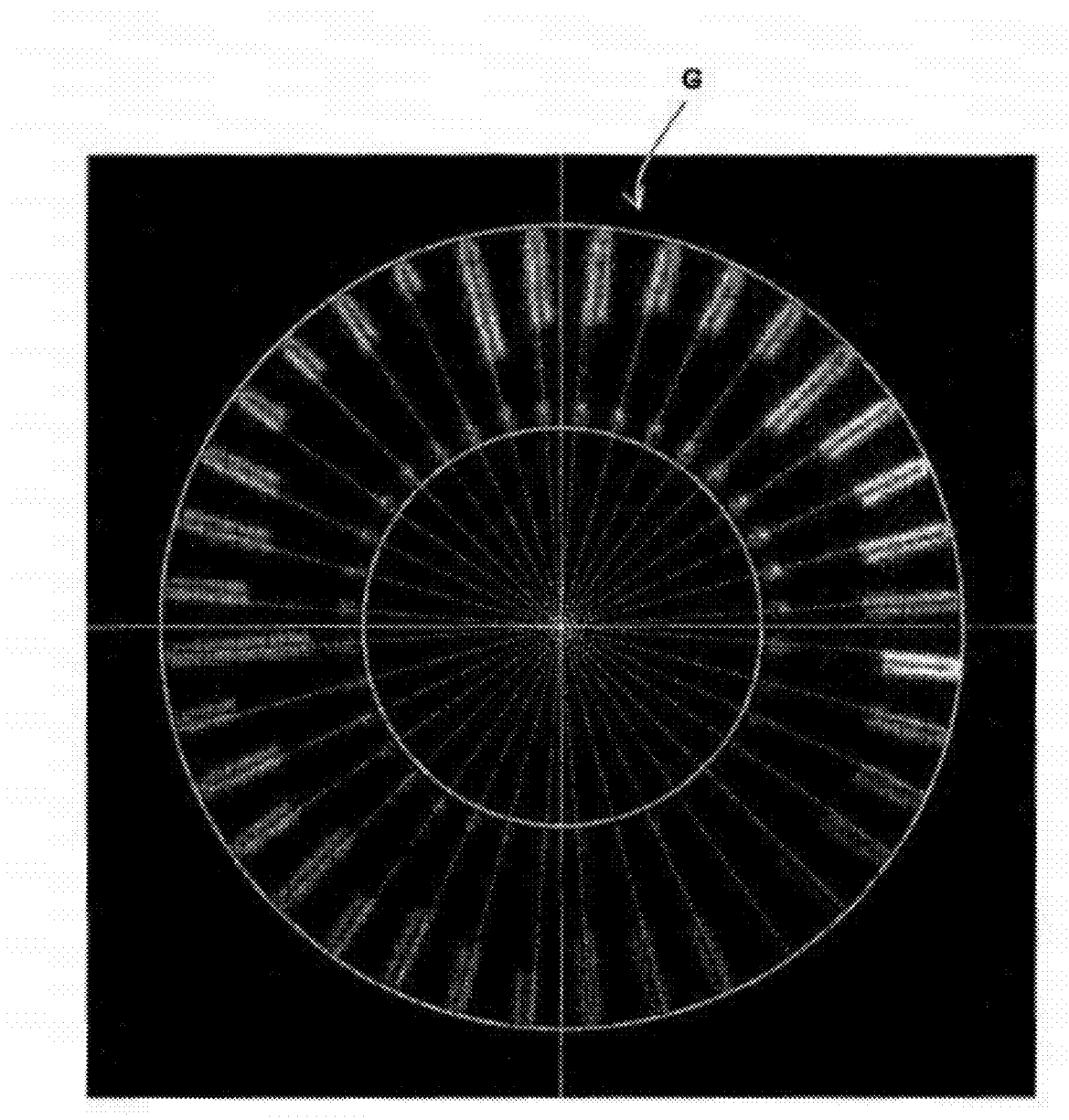
FIG. 10 is a diagram in which each example of the guide is appended to an IP image.

Therefore, a guide based on the design information of the container (here, disc 24; see FIG. 1, 3, or 4) is appended to the measurement information image (here, the IP image) and displayed. Each example of the guide will be described with reference to FIGS. 8 to 10. FIGS. 8 to 10 are diagrams in which each example of the guide is appended to the IP image. In FIG. 8, a crossed-line guide passing through the central position of the disc 24 is appended to the IP image as a guide G. In FIG. 9, a circular guide (a circular guide of the same size as the disc 24 and a circular guide similar to this circular guide) is appended to the IP image as a guide G in addition to the crossed-line guide described above. In FIG. 10, a linear guide is appended to the IP image as a guide G in addition to the crossed-line guide and the circular guide described above.

Figure 11:
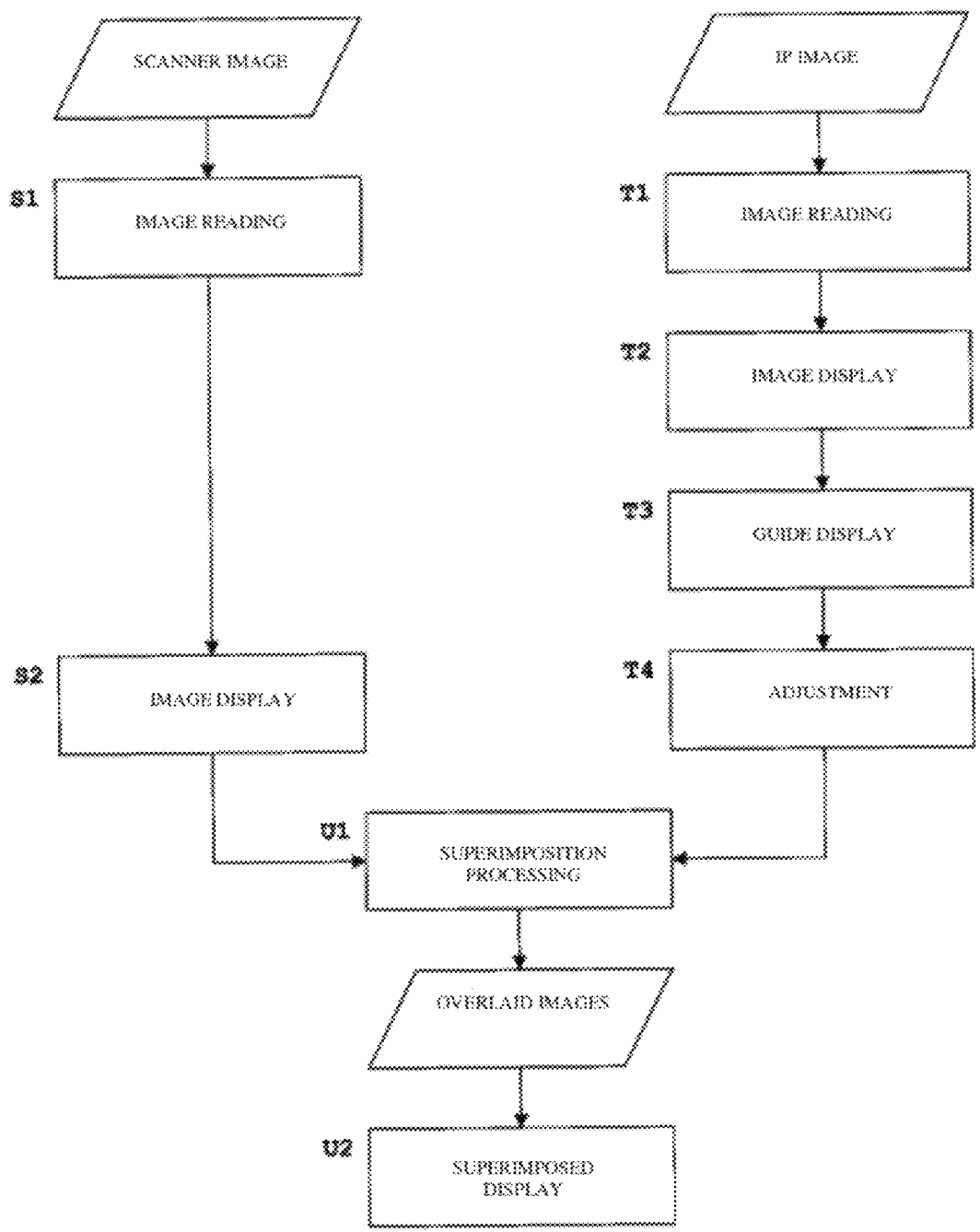
FIG. 11 is a flowchart illustrating the flow of a series of processes in the embodiment.

Next, a series of processes will be described with reference to FIG. 11 in combination with FIGS. 8 to 10. FIG. 11 is a flowchart illustrating the flow of the series of processes in the embodiment.

First, an IP image is obtained from the imaging plate IP (see FIG. 1) via the reading part 31 (see FIG. 1 or 2), and a scanner image is obtained from the flat head scanner of the imaging part 34 (see FIG. 2, 3, or 5). In addition, since the design information of the container (disc 24 in this embodiment; see FIG. 1, 3, or 4) is known in advance, this design information is written into and stored in the design information memory 37B (see FIG. 5) as a circle of the same size as the disc 24, a circle with a radius equal to the distance from the center of the disc 24 to the end of the folded portion, a circle with a radius equal to the distance to the inside end of the flow path inlets 25 (see FIG. 1 or 4) of the disc 24, the number (36 in this embodiment) or angle (10° in this embodiment) of the U-shaped flow paths 26 (see FIG. 1 or 4) consisting of two linear grooves and folded portions, and the crossed lines consisting of a line passing through the central position of the disc 24 and a line orthogonal to this line passing through the central position.

(Step S1) Image Reading

The second reading part 36B (see FIG. 5) reads the scanner image obtained by the imaging part 34 (see FIG. 2, 3, or 5).

In addition, in order to extract the region of interest, the controller 38 (see FIG. 5) may intensify the contour of the scanner image read in step S1 and output a contour-intensified image as necessary. The contour intensifying processing that is performed may be contour intensifying processing based on a first derivation for determining the difference between a pixel of interest and surrounding pixels thereof, as typified by Sobel filter processing or Prewitt filter processing, for example, or contour intensifying processing based on a second derivation for further determining the difference relative to the difference between the pixel of interest and the surrounding pixels thereof, as typified by Laplacian filter processing or the like. These types of contour intensifying processing are well-known techniques, so explanations thereof will be omitted here.

(Step T1) Image Reading

On the other hand, the first reading part 36A (see FIG. 5) reads the IP image obtained by the imaging plate IP (see FIG. 1) via the reading part 31 (see FIG. 1 or 2). The order of step S1 described above and this step T1 is not particularly limited. Step T1 may be performed first, step S1 may be performed first, or steps S1 and T1 may be performed simultaneously in parallel.

(Step S2) Image Display

The scanner image read in step S1 is displayed on each screen of the output monitor 50 (see FIG. 6). When the contour of the scanner image is intensified and a contour-intensified image is outputted, the contour-intensified image may be displayed on each screen of the output monitor 50 (see FIG. 6) instead of the scanner image. At this time, the scanner image (including the contour-intensified image) is subjected to reduction processing, and after the reduced scanner image is displayed on the reduced screen 53 illustrated in FIG. 6, the image may be displayed in an enlarged form on the main screen 51 illustrated in FIG. 6.

(Step T2) Image Display

On the other hand, the IP image read in step T1 is also displayed on each screen of the output monitor 50 (see FIG. 6). At this time, the IP image is subjected to reduction processing, and after the reduced IP image is displayed on the reduced screen 52 illustrated in FIG. 6, the image may be displayed in an enlarged form on the main screen 51 illustrated in FIG. 6.

(Step T3) Guide Display

When the IP image is displayed on the main screen illustrated in FIG. 6 in step T2, a guide G based on design information is appended to the IP image and displayed on the main screen 51, as illustrated in FIGS. 8 to 10. In order to append the guide G illustrated in FIG. 8 to the main screen 51 and display the image, design information is read out from the design information memory part 37B (see FIG. 5), and a crossed-line guide is appended to the IP image as a guide G based on the design information and displayed on the main screen 51, as illustrated in FIG. 8, or a crossed-line guide and a circular guide are appended to the IP image as a guide G based on the design information and displayed on the main screen 51, as illustrated in FIG. 9. Alternatively, a crossed-line guide, a circular guide, and a linear guide are appended to the IP image as a guide G based on the design information and displayed on the main screen 51, as illustrated in FIG. 10. Although not illustrated in FIGS. 8 to 10, the shapes of the grooves (here, the U-shaped flow paths; see FIG. 1 or 4) of the disc 24 (see FIG. 1, 3, or 4) are known from the design information, so a guide with the same contour lines as the shapes of the grooves (here, a U-shaped guide) may be displayed. This step T3 corresponds to the guide display step in the present invention.

As described above, even if misalignment occurs between the IP image and the scanner image to be subjected to superimposition processing as a result of being inclined when imaged by the flat heat scanner, the IP image can be positioned easily based on the guide G. FIGS. 8 to 10 illustrate cases in which the IP image matches the guide G. At this time, no misalignment occurs even if the scanner image is subjected to superimposition processing and displayed in a superimposed manner in steps U1 and U2 described below, but when the IP image causes misalignment in the guide G, the image is adjusted in step T4 described below.

(Step T4) Adjustment

When the IP image causes misalignment in the guide G, at least one of either the IP image or the guide G is moved and adjusted on the display screen, or the size of one or the other is adjusted on the display screen. The adjustment is made using the input part 39 (see FIG. 5). The adjustment may be made by grouping the respective guides G from the output monitor 50 illustrated in FIG. 6 and dragging and moving the grouped guides (in the central positions or contour positions thereof, for example) so as to match the IP image, by individually dragging and moving the guides G on the display screen so as to match the IP image, or by aligning the pointer to the contour portions of the guides G and adjusting the sizes of the guides G by reducing or expanding the guides G. Of course, the IP image may be moved and adjusted on the display screen, or the size of the IP image may be adjusted on the display screen. Alternatively, both may be moved and adjusted on the display screen, or the sizes of both may be adjusted on the display screen. In addition, the input part 39 may consist of a touch panel of the output monitor 50 so that the adjustment may be made by directly touching the IP screen or guide to be adjusted on the touch panel of the output monitor 50. This step T4 corresponds to the image/guide adjusting step in the present invention.

The order of steps S2 and T2 to T4 described above is not particularly limited. Steps T2 to T4 may be performed first, step S2 may be performed first, or steps S2 and T2 to T4 may be performed simultaneously in parallel.

(Step U1) Superimposition Processing

The controller 38 (see FIG. 5) performs superimposition processing by overlaying the scanner image displayed in step S2 and the IP image adjusted in step T4.

(Step U2) Superimposed Display

The superimposed image (designated as the "overlaid image" in FIG. 11) is displayed on each screen of the output monitor 50 (see FIG. 6). At this time, the superimposed image is subjected to reduction processing, and after the reduced image is displayed on the reduced screen 54 illustrated in FIG. 6 following superimposition processing, the image may be displayed in an enlarged form on the main screen illustrated in FIG. 6.

In addition, when the disc 24 (see FIG. 1, 3, or 4) is inclined for each fixture 61 (see FIG. 7) at the time of imaging with the flat head scanner, misalignment occurs in the scanner image with respect to the guide G as well, so an adjustment should be made in the same manner as in step T4 at the time of superimposed display. Since the adjustment has already been made between the IP image and the guide G in step T4, the scan image may be moved and adjusted on the display screen, or the size of the scan image may be adjusted on the display screen. At this time, superimposed display may be realized by eliminating the display of the IP image so as to display only the guide G and the scan image and then once again displaying the IP image after adjustment. When an adjustment is first made between the guide G and the scan image at the stage of the image display of step S2 described above, it is unnecessary to make an adjustment at the stage of this step U2.

With the display device 35 used in the measurement system of this embodiment, by providing a guide display (the main display screen 51 in this embodiment) for displaying a measurement information image (the IP image in this embodiment) having measurement information for radiation ($\beta$+ rays in this embodiment) contained in the liquid to be measured (blood in this embodiment) and appending a guide G, which is based on design information of the container (the disc 24 in this embodiment) housing the liquid (blood) to be measured, to the measurement information image (IP image) and displaying the image, a guide G is appended to a measurement information image (IP image) in which a guide is not originally reflected, which makes it possible to visually discern a reference position (central position of the disc 24 in this embodiment) based on design information in the measurement information image (IP image). As a result, it is possible to facilitate positioning in the measurement information image (IP image) based on the guide G indicating the reference position (central position of the disc 24).

In addition, with the display method and the display program 37A of this embodiment, a measurement information image (the IP image in this embodiment) having measurement information for radiation ($\beta$+ rays in this embodiment) contained in the liquid to be measured (blood in this embodiment) is displayed in step T3, and a guide G, which is based on design information of the container (the disc 24 in this embodiment) housing the liquid (blood) to be measured, is appended to the measurement information image (IP image) and displayed so that a reference position (central position of the disc 24 in this embodiment) based on design information can be visually discerned in the measurement information image (IP image). As a result, it is possible to facilitate positioning in the measurement information image (IP image) based on the guide G indicating the reference position (central position of the disc 24).

The display device 35 of this embodiment is equipped with a superimposition processor (the controller 38 in this embodiment) for performing superimposition processing by overlaying the measurement information image (the IP image in this embodiment) and the morphological information image (the scanner image in this embodiment) having morphological information of the liquid to be measured (blood in this embodiment), and the guide display (the main screen 51 in this embodiment) preferably appends the guide G to the image prior to superimposition processing and displays the image. By appending the guide G to the image prior to superimposition processing and displaying the image, it is possible to accurately realize the superimposition processing of the measurement information image (IP image) and the morphological information image (scanner image) based on the guide G.

The display device 35 of this embodiment is preferably equipped with an image/guide adjustor (the input part 39 in this embodiment) for moving and adjusting at least one of either the measurement information image (the IP image in this embodiment) or guide G on the display screen or adjusting the size of one or the other on the display screen.

In addition, the display method of this embodiment preferably includes step T4 for moving and adjusting at least one of either the measurement information image (the IP image in this embodiment) or guide G on the display screen or adjusting the size of one or the other on the display screen. By making adjustments on the display screen, it is possible to relatively align the measurement information image (IP image) with respect to the guide G, and even in superimposition processing with the morphological information image described above (the scanner image in this embodiment), superimposition processing can be performed accurately after the positions are aligned.

Further, when the container is circular (the disc 24 in this embodiment), as in the case of this embodiment, the guide G is preferably a circular guide or a guide with a shape similar to a circular shape (generally called a "circular guide"), as illustrated in FIG. 9 or 10. By using a guide (circular guide) that conforms to the shape of the circular container (here, the disc 24), it is possible to even further facilitate positioning in the measurement information image (the IP image in this embodiment).

In addition, when the grooves (flow paths; U-shaped flow paths 26 in this embodiment) of the container (the disc 24 in this embodiment) provided in order to house the liquid to be measured (blood in this embodiment) extend linearly, as illustrated in FIG. 4, the guide G is preferably a guide having a linear shape (linear guide) with the same angles as the linear grooves of the container (disc 24), as illustrated in FIG. 10. Since the number (36 in FIG. 4) of grooves (U-shaped flow paths 26) or the angles thereof (10° in FIG. 4) are known from the design information of the container (disc 24), using a guide (linear guide) that conforms to the shape of the linear grooves (U-shaped flow paths 26) makes it possible to further facilitate positioning in the measurement information image (IP image).

Further, the guide G may also be a guide (here, a U-shaped guide) with a contour of the same shape as the grooves (the U-shaped flow paths 26 in this embodiment) of the container (the disc 24 in this embodiment) provided in order to house the liquid to be measured (blood in this embodiment). By using a guide G that conforms to the contour of the grooves (U-shaped flow paths 26), it is possible to further facilitate positioning in the measurement information image (IP image).

In addition, the guide G may also be a linear guide (here, a crossed-line guide) passing through the central position of the container (disc 24 in this embodiment), as illustrated in FIGS. 8 to 10. In this case, positioning in the measurement information image (IP image) can be performed using the central position as a reference position.

The present invention is not limited to the embodiment described above and may be modified as described below.

(1) The embodiment described above was described using blood as an example of the liquid to be measured, but the liquid is not limited to blood as long as the liquid is to be measured, and the liquid may be a liquid contained in a radioactive substance, a light-emitting substance, or a fluorescent agent or a mixture used in an analysis device. In addition, the liquid to be measured may also be a liquid to be centrifuged.

(2) In the embodiment described above, the measurement information image was an IP image having measurement information for radiation (β+ rays in this embodiment) obtained from the imaging plate IP, but this image is not necessarily limited to an IP image as long as it is a measurement information image having measurement information for emitted light contained in the liquid to be measured, light generated from a fluorescent substance, or radiation contained in the liquid to be measured, and the image may be, for example, a measurement information image obtained by counting the light (photons) or radiation directly.

(3) In the embodiment described above, the morphological information image was a scanner image obtained from the flat head scanner of the imaging part 34, but the image is not necessarily limited to a scanner image as long as it is a morphological information image having morphological information of the liquid to be measured, and the image may be, for example, a morphological information image obtained with a radiation imaging means consisting of a radiation irradiator and a radiation detector.

(4) In the embodiment described above, the guide was based on the design information of the container (the disc 24) in this embodiment, but the guide may also be based on region information of the region to be measured serving as the specific position to be measured. For example, the region information of the container housing the liquid to be measured (blood in this embodiment) may be read and imaged by the flat head scanner of the imaging part 34, and a guide based on this region information may be appended to the measurement information image (the IP image in this embodiment) and displayed. By appending a guide based on the region information to be measured serving as the specific position to be measured to the measurement information image (IP image) and displaying the image, the specific position (for example, the housing position of the liquid) can be visually discerned in the measurement information image. As a result, it is possible to facilitate positioning in the measurement information image (IP image) based on the guide indicating the specific position. In addition, the guide may also be displayed by combining a specific position and a reference position based on design information.

(5) In the embodiment described above, the reference position was the central position of the container (the disc 24 in the embodiment), but the reference position is not limited to the central position. For example, the position may be any position such as a point at the end of a groove (flow path) of the container.

(6) In the embodiment described above, the measurement information image (the IP image in this embodiment) and the morphological information image (the scanner image in this embodiment) were overlaid and subjected to superimposition processing, but the morphological information image is not absolutely necessary. The guide may also be appended to an image of the measurement information image (IP image) alone and displayed.

(7) In the embodiment described above, adjustments were made by moving and adjusting at least one of either the measurement information image (the IP image in this embodiment) or the guide on the display screen or adjusting the size of one or the other on the display screen, but it is not absolutely necessary to make adjustments when the positions of the measurement information image and the guide are in alignment relative to one another.

(8) In the embodiment described above, the container was a disc for performing centrifugation, but when the liquid to be measured is not a liquid to be centrifuged, the container is not limited to a disc as long as the container houses the liquid. The container may also be a square plate, a polygonal plate, or the like.

(9) In the embodiment described above, a plurality of U-shaped flow paths 26 formed in the radial direction were provided by performing groove machining radially along the radial direction of the disc 24, but it is not absolutely necessary to dispose the flow paths radially. For example, the flow paths may also be disposed parallel to one another.

(10) When the container has a non-circular shape, as in the modified example (8) described above, a guide that conforms to this shape may be used. For example, when the container is a square plate, a square guide or a guide with a shape similar to a square shape may be used, and when the container is a polygonal plate, a polygonal guide or a guide with a shape similar to a polygonal shape may be used. In addition, it is unnecessary to use a guide that conforms to the shape of the container, and a guide that conforms to the contour of the grooves (flow paths) of the container or a guide that conforms to a line connecting the end parts of the respective grooves (flow paths) may be used. For example, a guide that conforms to the contour of grooves (flow paths) disposed parallel to one another, as in the modified example (9), may be used, or a guide that conforms to a line connecting the end parts of the respective grooves (flow paths) disposed parallel to one another may be used.

(11) In the embodiment described above, the grooves (flow paths) of the container were U-shaped flow paths extending linearly, but a guide that conforms to the shape of the grooves (flow paths) may also be used. For example, when the grooves (flow paths) extend in a curved shape, a curved guide may be used.

(12) In the embodiment described above, a crossed-line guide consisting of two linear guides orthogonal to one another was used as a linear guide passing through the central position of the container (the disc 24 in this embodiment), but it is not absolutely necessary to use a crossed-line guide. One linear guide may be used, or three or more linear guides may be used. Alternatively, two linear guides crossing one another diagonally may be used. In addition, when the respective grooves (flow paths) are provided asymmetrically, the guide does not necessarily need to be a linear guide passing through the central position of the container.

(13) In the embodiment described above, a fixture 61 that fixes, positions, and supports the container (the disc 24 in this embodiment) was provided, but it is not absolutely necessary to provide the fixture 61. For example, the orientations of the images to be superimposed may be aligned by providing depressions in the disc 24 itself as illustrated in FIG. 4 or providing notches or protuberances in the disc 24 itself and using the depressions, notches, protuberances, or the like as a reference. In addition, superimposition processing may also be performed after aligning the orientations by attaching members having different transmittances for light or radiation at prescribed locations of the disc 24 as markers and using the marker portions as a reference in a captured image.

(14) In the embodiment described above, the measurement system was described using automatic blood collection with a blood collection device 10 as an example, but the liquid sampling method is not limited to an automatic liquid sampling device. A method in which the liquid is dropped into the U-shaped flow paths 26 of the disc 24 by means of the skill of the operator may also be used.

(15) In the embodiment described above, the guide G was appended to a (measurement information) image (IP image) prior to superimposition processing and displayed, but the guide G may be overlaid with the morphological information image (scanner image) directly and displayed without being eliminated after the guide G is appended to the image prior to superimposition processing and displayed.

EXPLANATION OF REFERENCES

24 . . . disc
26 . . . U-shaped flow path
35 . . . display device
37A . . . display program
38 . . . controller
39 . . . input part
51 . . . main screen
G . . . guide

What is claimed is:

1. A measurement system for measuring light emitted from a liquid to be measured, comprising:
    an optical measurement means that obtains measurement information by measuring the light emitted from the liquid to be measured;
    an imaging means for obtaining a morphological image of the liquid to be measured and of a container housing the liquid to be measured, the morphological image including a plurality of flow paths of the liquid to be measured; and
    a guide display configured to:
        display a measurement information image having the measurement information for the light emitted from the liquid to be measured,
        draw a guide to indicate a reference position based on design information of the container housing the liquid to be measured,
        append the guide to the measurement information image,
        superimpose the morphological information image on the measurement information image with the guide; and
        display an image comprising the measurement information image, the guide, and the morphological information image;
    wherein the guide aligns the measurement information for the light emitted from the liquid with respect the flow paths of the morphological image whereby the light emitted from the liquid within the flow paths is identified.

2. The measurement system according to claim 1, further comprising an image/guide adjustor for moving or adjusting at least one of either the measurement information image or the guide on a display screen.

3. The measurement system according to claim 1, wherein the container has a circular shape; and wherein the guide has a circular shape corresponding to the circular shape of the container.

4. The measurement system according to claim 1, wherein the container further comprises linear grooves oriented at an angle and configured to house the liquid to be measured, and wherein the guide is a linear guide having radial lines oriented at the same angle as the linear grooves.

5. The measurement system according to claim 1, wherein the container further comprises grooves configured to house the liquid to be measured, and wherein the guide has a contour corresponding to a contour of the grooves.

6. The measurement system according to claim 1, wherein the guide comprises a line passing through a central position of the container.

7. The measurement system according to claim 1, wherein the liquid to be measured is blood, and the light emitted from the liquid to be measured indicates a radiation concentration in the blood.

8. A display method for displaying measurement data obtained by measuring light emitted from a liquid to be measured, the method comprising:
    receiving measurement information obtained by measuring the light emitted from the liquid to be measured;
    receiving a morphological image of a morphological image of the liquid to be measured and of a container housing the liquid to be measured, the morphological image including a plurality of flow paths of the liquid to be measured;
    displaying a measurement information image having the measurement information for the light emitted from the liquid to be measured,
    displaying a morphological information image comprising the morphological information;
    drawing a guide to indicate a reference position based on design information of the container housing the liquid to be measured,
    appending the guide to the measurement information image,
    superimposing the morphological information image on the measurement information image with the guide, and
    displaying an image comprising the measurement information image, the guide, and the morphological information image;
    wherein the guide facilitates alignment of the measurement information for the light emitted from the liquid with respect the flow paths of the morphological image whereby the light emitted from the liquid within the flow paths is identified.

9. The display method according to claim 8, further comprising moving or adjusting at least one of either the measurement information image or the guide on a display screen.

10. The method according to claim 8, wherein the liquid to be measured is blood, and the light emitted from the liquid to be measured indicates a radiation concentration in the blood.

11. A non-transitory computer readable medium including a display program operable to cause a computer to execute a series of processes for displaying measurement data obtained by measuring light emitted from a liquid to be measured, the series of processes comprising:
    receiving measurement information obtained by measuring the light emitted from the liquid to be measured;
    receiving a morphological image of a morphological image of the liquid to be measured and of a container housing the liquid to be measured, the morphological image including a plurality of flow paths of the liquid to be measured;
    displaying a measurement information image having the measurement information for the light emitted from the liquid to be measured,
    drawing a guide to indicate a reference position based on design information of the container housing the liquid to be measured,
    appending the guide to the measurement information image, superimposing the morphological information image on the measurement information image with the guide, and displaying an image comprising the measurement information image, the guide, and the morphological information image;

wherein the guide facilitates alignment of the measurement information for the light emitted from the liquid with respect the flow paths of the morphological image whereby the light emitted from the liquid within the flow paths is identified.

12. The non-transitory computer readable medium according to claim 11, wherein the liquid to be measured is blood, and the light emitted from the liquid to be measured indicates a radiation concentration in the blood.

* * * * *